(12) United States Patent
Baumann et al.

(10) Patent No.: US 9,927,415 B2
(45) Date of Patent: Mar. 27, 2018

(54) OIL QUALITY SENSOR AND FRYER WITH SUCH OIL QUALITY SENSOR

(71) Applicant: WTW Wissenschaftlich-Technische Werkstätten GmbH, Weilheim (DE)

(72) Inventors: Michael Baumann, Neuburg (DE); Klaus Beyer, Ingolstadt (DE); Thomas Ottenthal, Augsburg (DE)

(73) Assignee: XYLEM ANALYTICS GERMANY GMBH, Weilheim (DE)

( * ) Notice: Subject to any disclaimer, the term of this patent is extended or adjusted under 35 U.S.C. 154(b) by 80 days.

(21) Appl. No.: 14/677,229

(22) Filed: Apr. 2, 2015

(65) Prior Publication Data

US 2015/0285777 A1 Oct. 8, 2015

(30) Foreign Application Priority Data

Apr. 4, 2014 (DE) .......................... 10 2014 104 843

(51) Int. Cl.
*F17D 3/05* (2006.01)
*G01N 33/03* (2006.01)
(Continued)

(52) U.S. Cl.
CPC .......... *G01N 33/03* (2013.01); *A47J 37/1266* (2013.01); *G01N 27/223* (2013.01);
(Continued)

(58) Field of Classification Search
CPC ....................................................... F17D 3/05
(Continued)

(56) References Cited

U.S. PATENT DOCUMENTS 3,739,265 A * 6/1973 Skildum ............ G01R 27/2605
324/673
4,105,334 A * 8/1978 Halko ................ G01N 21/8507
250/574
(Continued)

FOREIGN PATENT DOCUMENTS

CH 692826 A5 11/2002
CN 202837286 U 3/2013
(Continued)

OTHER PUBLICATIONS

Baumannn, Michael, Oil Quality Sensor and Deep Fryer with such an Oil quality Sensor, European International Search Report, EP15162215, dated Sep. 10, 2015, 5 pages.*
(Continued)

*Primary Examiner* — Clayton E Laballe
*Assistant Examiner* — Kevin Butler
(74) *Attorney, Agent, or Firm* — Dority & Manning, P.A.

(57) ABSTRACT

An oil quality sensor to determine the quality of deep-frying oil by measuring the capacitance of the deep-frying oil in a deep fryer includes a housing and a hollow space in the housing through which the deep-frying oil is guided. An inlet opening introduces deep-frying oil to the hollow space, and a drain opening guides the deep-frying oil out of the hollow space. A first bent electrode extends along the hollow space, and a second bent electrode extends along the hollow space and is arranged opposite the first electrode, in which case the two electrodes form a capacitor and deep-frying oil is guided through the space formed between these two electrodes to measure its capacitance. A first temperature sensor measures the temperature of the oil used for deep frying that needs to be measured. An evaluation unit records the measured capacitance of the capacitor and the measured temperature, digitalizes these measured values, and calculates the polar fractions in the deep-frying oil, in which case
(Continued)

these polar fractions are a criterion for the quality of the deep-frying oil.

19 Claims, 2 Drawing Sheets

(51) Int. Cl.
    *G01N 27/24* (2006.01)
    *A47J 37/12* (2006.01)
    *G01N 27/22* (2006.01)
    *G01F 23/26* (2006.01)
    *G01N 11/08* (2006.01)
    *B01L 3/02* (2006.01)
    *F16L 41/08* (2006.01)

(52) U.S. Cl.
    CPC ........... *G01N 27/226* (2013.01); *G01N 27/24* (2013.01); *B01L 3/0241* (2013.01); *F16L 41/08* (2013.01); *F17D 3/05* (2013.01); *G01F 23/268* (2013.01); *G01N 11/08* (2013.01)

(58) Field of Classification Search
    USPC ........................................................ 73/64.56
    See application file for complete search history.

(56) References Cited

U.S. PATENT DOCUMENTS

| | | | | |
|---|---|---|---|---|
| 4,470,008 A * | 9/1984 | Kato | ..................... | G01F 23/263 222/639 |
| 5,818,731 A * | 10/1998 | Mittal | ................. | A47J 37/1266 702/22 |
| 6,250,152 B1 | 6/2001 | Klein et al. | | |
| 6,600,306 B1 * | 7/2003 | Pernot | ................. | A47J 37/1266 324/423 |
| 7,504,836 B2 * | 3/2009 | Chambon | ........... | A47J 37/1266 324/686 |
| 8,257,976 B2 * | 9/2012 | Wei | ..................... | G01N 21/643 422/420 |
| 8,325,345 B2 * | 12/2012 | Mahmoodi | ............ | G01N 21/78 250/458.1 |
| 8,497,691 B2 * | 7/2013 | Behle | .................. | A47J 37/1223 324/663 |
| 8,847,120 B2 * | 9/2014 | Burkett | ............... | A47J 37/1266 219/439 |
| 2009/0193873 A1 * | 8/2009 | Nakamura | ............ | F02D 33/003 73/31.05 |
| 2009/0309619 A1 * | 12/2009 | Behle | .................. | A47J 37/1223 324/698 |
| 2011/0084708 A1 * | 4/2011 | Yu | .......................... | G01N 33/03 324/658 |
| 2012/0182030 A1 * | 7/2012 | Calciolari | .............. | G01N 27/07 324/693 |
| 2013/0036916 A1 * | 2/2013 | Burkett | ............... | A47J 37/1266 99/330 |
| 2015/0027205 A1 * | 1/2015 | Brugger | .............. | A47J 37/1266 73/53.01 |
| 2015/0285777 A1 * | 10/2015 | Baumann | ............... | G01N 27/24 73/64.56 |
| 2015/0374173 A1 * | 12/2015 | McGhee | ................ | G01N 33/03 99/330 |
| 2016/0033463 A1 * | 2/2016 | Robertson | .............. | G01N 33/03 426/231 |

FOREIGN PATENT DOCUMENTS

| | | |
|---|---|---|
| DE | 19511556 C1 | 7/1996 |
| DE | 202005007144 U1 | 7/2005 |
| DE | 100 15 156 B4 | 3/2012 |

OTHER PUBLICATIONS

Gloria Márquez-Ruiz, Determination of Polar Compounds in Used Frying Oils and Fats by Adsorption Chromatography, AOCS Lipid Library, Jun. 10, 2009, pp. 7.*

Jose Arnaldo Gerde, Frying performance of soybean oils with reduced linolenate content and methods to monitor deteriorative changes, Iowa State University Digital Repository Retrospective Theses and Dissertations, 2006, pp. 8-12.*

M.C.Dobarganes,J.Velasco, and A.Dieffenbacher, Determination of Polar Compounds, Polymerized and Oxidized Triacylglycerols, and Diacylglycerols in Oils and Fats, Pure Applied Chem (IUPAC)., vol. 72, No. 8, pp. 1563-1575, 2000.*

Jose A. Gerde, Connie L. Hardy, Charles R. Hurburgh Jr, Pamela J. White, Rapid Determination of Degradation in Frying Oils with Near-Infrared Spectroscopy, J Amer Oil Chem Soc (2007) 84:519-522.*

E. Choe et al., Chemistry of Deep-Fat Frying Oils, Journal of Food Science vol. 00, Nr. 0, 2007, pp. 10.*

EPO, European Search Report EP15162215, EPO, dated Sep. 10, 2015, pp. 5.*

European Patent Office Search Report, dated Sep. 10, 2015.

* cited by examiner

OIL QUALITY SENSOR AND FRYER WITH SUCH OIL QUALITY SENSOR

FIELD OF THE INVENTION

The invention refers to an oil quality sensor to determine the quality of deep-frying oil by measuring the capacitance of the deep-frying oil in a deep fryer.

BACKGROUND

Devices that measure deep-frying oil quality are known in which a deep-frying oil sample is taken from the deep fryer basin and the deep-frying oil quality is measured in a measuring instrument outside the deep fryer by means of a capacitor. This device takes advantage of the dielectric constant of the deep-frying oil, which changes as it ages. Using a correlation function, the polar fractions of the deep-frying oil can be calculated from the change of the dielectric constant.

It is furthermore known from DE 199 18 213 (now DE 100 15 516) that the quality of deep-frying oil can be measured with a device held in one hand. To carry out the measurement, the operator grasps the housing in which the electronic measurement system is arranged. On the underside of the housing, a metal pipe is fixed and an exposed interdigital capacitor is arranged on its free end. The capacitor is connected to the electronic measurement system with the electric wires running in the metal pipe and a part of this electronic system is also housed in the metal pipe. Apart from the capacitance (and thereby of the dielectric constant), the temperature of the deep-frying oil is also measured with the known device because the dielectric constant depends not only on the quality of the deep-frying oil, i.e. of the polar fractions, but also very much on the temperature of the deep-frying oil. The measured oil temperature enters directly in the calculation of the polar fractions. Therefore, the quantity of the polar fractions in the deep-frying oil—and thus the deep-frying oil quality—can be inferred directly from the measured values of the capacitance and temperature in the calculation of the polar fractions.

Moreover, it is known from U.S. Pat. No. 8,497,691 B1 that a stationary oil quality sensor is arranged in a filtering cycle, in a return flow or in a deep fryer tank. Like the manual measuring device mentioned above, the oil quality sensor has an interdigital capacitor.

The disadvantage in these two devices mentioned first is that they always demand the active participation of the operator. In the hectic environment of a fast food restaurant, however, the measuring task can often be forgotten. Also, the staff must handle the portable device rather carefully because otherwise the capacitor can be damaged if it touches the deep fryer basin, for example. Regarding its measuring precision, the known stationary oil quality sensor does not meet the highest requirements.

SUMMARY OF THE INVENTION

It is a task of this invention to make an oil quality sensor available that ensures easier and safer handling, on the one hand, and high measuring precision on the other hand. Additional objects and advantages of the invention will be set forth in part in the following description, or may be obvious from the description, or may be learned through practice of the invention.

The advantages of the invention can be seen especially in the fact that the oil quality sensor, which can be installed permanently in the deep fryer, is equipped with a capacitor, and the deep-frying oil is guided through its two electrodes. Thus, the oil quality sensor can be operated as a flow sensor or when the deep-frying oil is standing. By leading the deep-frying oil through an elongated capacitor, the measuring precision is increased significantly compared to an interdigital capacitor.

According to an especially preferred embodiment, the capacitor is executed as cylinder capacitor. Here, the second (external) electrode surrounds the first (internal) electrode and in doing so, creates a space through which the deep-frying oil (as dielectric material of the capacitor) can be guided through. In this case, integration of the oil quality sensors in the existing oil cycle is possible very easily. Additionally, the elongated design of the capacitor as a cylinder capacitor creates a large measuring surface that allows very precise measurements. It is also possible to adapt the line cross-section of the cylinder capacitor to the remaining lines of the deep fryer, so that the oil quality sensor according to the invention causes no pressure changes, turbulence or other unwelcome effects.

Another advantageous alternative provides the execution of the capacitor as a tube capacitor, in which the two electrodes are preferably executed largely as equal-sized half shells that form an almost closed circle together in cross section. The concave surfaces of these two electrodes lie opposite one another after creating a space, in which case the deep-frying oil is guided here through this space too. The advantages of a tube capacitor are comparable to those of a cylinder capacitor.

If the deep-frying oil flows through the oil quality sensor according to the invention, in most cases the deep-frying oil will have another temperature than the oil quality sensor itself. Since the deep-frying oil reaches the oil quality sensor from a hot and deep fryer basin, it is usually considerably warmer than the oil quality sensor itself. For this reason, a temperature gradient between the external side of the oil quality sensor and the internal electrode will form in a cylinder capacitor, in which case the temperature of the deep-frying oil between the external and internal electrode is not homogenous. Due to this temperature gradient, a preferred embodiment is characterized by the fact that a second temperature sensor is provided that is placed in another part away from the first temperature sensor. Advantageously, one of the temperature sensors is close to the first electrode or on it, while the other temperature sensor is placed close to the second electrode or on it. Especially preferable is a combined temperature calculated from the measured values determined by the evaluation unit from the two temperature sensors, preferably an average effective temperature, which is then used by the evaluation unit to determine the polar fractions.

If the capacitor is executed as a cylinder capacitor, a corresponding advantageous embodiment provides a temperature sensor inside a hollow section of the first, internal electrode and/or the other temperature sensor is arranged on the external side of the second, external electrode facing away from the first electrode. As a result of this, the temperature gradient can advantageously be accounted for if the temperature sensors for the deep-frying oil are protected and placed simultaneously outside the flow-through area. Naturally, it is also possible to arrange one or two temperature sensors in the flow-through area of the deep-frying oil.

Incidentally, it is not ruled out that a third temperature sensor (or additional ones) to increase even more the calculation precision of the polar fractions can be placed on different parts of the oil quality sensor.

It must be pointed out here that the evaluation unit can also execute its task through various distributed electronic parts, i.e. the evaluation unit does not have to be housed in just one single housing or board.

According to a practical embodiment, a shield electrode is provided around the electrodes to protect them from external interfering signals. This can increase measurement accuracy and reproducibility considerably.

It has proven to be especially advantageous if the middle axis of the inlet and/or drain opening runs at an angle, preferably at an angle of 90°, to the longitudinal axis of the capacitor or hollow space, i.e. ending in the hollow space under an angle greater than 0°. If both—the inlet and drain opening—would run in the axial direction of the capacitor, the electrical wires for the two electrodes and for the temperature sensor(s) could be connected relatively easily. By bending at least the middle axis of the inlet opening or drain opening with respect to the longitudinal axis of the capacitor, the electric wires can be led from the side of the bent inlet or drain opening. Here, these electric wires run preferably and largely in axial direction of the capacitor or hollow space (i.e. in its rear extension), which does not obstruct such a laying of the electrical wires owing to the bending mentioned above.

Accordingly, a chamber is attached to the rear, preferably to a front side of the hollow space, and this chamber serves to house the electronic measurement system, especially the evaluation unit. In this case, the electronic measurement system is connected to the electric wires leading to the two electrodes and the temperature sensor(s). Moreover, a digital interface is preferably arranged on or in a chamber, which is connected to the electronic measurement system. Signals—especially the measured values and/or the calculated values for the polar fractions and/or a signal indicating oil quality (e.g. "green" for "oil quality OK" and "red" for "deep-frying oil must be changed")—can be emitted via the interface. The electronic measurement system can also be programmed through the interface (e.g. the measurement cycle can be set).

In the embodiment of a bent middle axis of the inlet and/or drain opening described above, the middle axis of the other opening (i.e. the middle axis of the drain or inlet opening) runs preferably parallel and very preferably coaxial to the longitudinal axis of the capacitor. The result is a compact design with outstanding use of space, flow-through of the oil quality sensor and connection options, both with regard to the flow-through lines carrying the deep-frying oil and the electrical wires.

According to what has been said above, in a specific and advantageous embodiment of the oil quality sensor, the middle axis of the inlet opening runs at an angle, preferably at an angle of 90°, to the longitudinal axis of the capacitor, while the middle axis of the drain opening runs parallel and preferably coaxial to the longitudinal axis of the capacitor. Here, the electrical wires leading to the two electrodes and/or the temperature sensor(s) come from the side of the bent inlet opening of the oil quality sensor, preferably and largely in the axial direction of the hollow space of the oil quality sensor.

It is useful if the oil quality sensor according to the invention has an electronic storage unit where correlation functions are stored. The latter display the correlation between the measured capacitance values and the different types of oil, which are used—even internationally—for deep frying the goods to be deep fried (e.g. French fries, chicken pieces, etc.). Depending on the type of oil selected, the evaluation unit accesses these correlation functions with the correspondingly stored correlation values for calculating the polar fractions while using the measured capacitance and temperature. Thus, accurate quality assessments for many different deep-drying oil types can be obtained. The oil quality sensor according to the invention can therefore be used universally in a flexible way.

The invention comprises also a deep fryer into which an oil quality sensor according to the invention and as described above is integrated accordingly. This deep fryer is easy to operate, the oil quality sensor is protected by the integration, and its design allows a very good, safe, easy and very precise determination of the deep-frying oil quality.

Various places can be considered for installing the oil quality sensor in the filtering device. For example, the oil quality sensor can be integrated to the oil cycle, where the filtering device is also placed. Here, the oil quality sensor lends itself to be arranged downstream from the filtering device so no deep-frying remainders, etc. can accumulate in the oil quality sensor. An alternative provides a secondary cycle (measurement cycle), in which the oil quality sensor is built in.

It is advantageous if the deep-frying oil flows uniformly through without generating turbulence when the oil quality sensor has a flow-through cross section that does not deviate more than 25% of the flow-through cross section of the lines leading to the oil quality sensor and away from the oil quality sensor. Preferably, the flow-through cross sections have largely the same size.

It is especially preferable if the oil quality sensor is arranged in such a way in the deep fryer that the longitudinal axis of the capacitor forms an angle within the range of 20° to 90°, preferably larger than 30°, with the horizontal, in which case the drain opening points preferably upward. This allows the accuracy of the measurements to be increased as follows: As soon as the sensor fills with oil, the oil quality can be determined through the capacitance and temperature. If this occurs while deep-frying oil is being pumped through the sensor, air bubbles and water that can possibly be in the oil flow can affect the measurement result. If the sensor is filled with a pump, the oil flow stops and a certain time is allowed to elapse so the air, water vapor and/or water in the deep-frying oil can leave the space between the two electrodes. The measurement result will then only be determined by the deep-frying oil. Air and water vapor can leave the above-mentioned space, for example, because these gaseous compounds can escape upward from the drain opening of the oil quality sensor. This is facilitated by mounting the oil quality sensor at an angle between 20° and 90°, preferably larger than 30°. Water can deposit in the oil quality sensor between the two electrodes, below the above-mentioned spaces.

The invention also comprises a corresponding discontinuous measurement method, whereby after the oil quality sensor is serviced by filling it with deep-frying oil until air, water vapor, and/or water have escaped from the space between the electrodes or the oil quality sensor, in order to measure the capacitance. The slanted arrangement of the oil quality sensor is preferred here, as described above.

With the oil quality sensor or deep fryer according to the invention, the presence of air in the filtering cycle can be recorded advantageously. If there is air in the filtering cycle, this will cause the deep-frying oil to age considerably faster, since oil oxidation is increased strongly. Therefore, air in the filtering cycle should be prevented or minimized as much as possible. To estimate whether there is (too much) air in the oil cycle, a continuous capacitance measurement is carried out while pumping takes place during filtering. This allows air bubbles to be detected by means of signal changes. The more air is in the system, the larger will be the measuring signal fluctuations during pumping. The evaluation unit detects and evaluates these signal fluctuations in order to forward them advantageously to a higher-ranking system (e.g. the control of the deep fryer) as measure of the air quantity. With this information, the control can notify the user or repairman, for example, so he can remedy the cause of the air accumulation in the system.

The oil quality sensor according to the invention can also be used as a fill level sensor because the difference in the signal between a filled and unfilled sensor is very clear. This can be used, for example, to stop the pump of a filtering device as soon as no more deep-frying oil is in the filtering tank, i.e. when all the oil has been pumped into the deep fryer basin. If according to this, it is detected that a threshold value of the measured capacitance is not reached or exceeded across a preferably specified time period, this can be transmitted to the deep fryer's control device, for example, which can then conclude from the threshold value not reached or exceeded that the oil flow through the oil quality sensor has been interrupted and induce the emission of the corresponding signal, e.g. an alarm or control signal to turn off the pump.

BRIEF DESCRIPTION OF THE DRAWINGS

The invention is described below in more detail by means of figures, wherein the same reference characters are used for the same or equivalent elements. Shown are.

DETAILED DESCRIPTION

Figures 1, 1A, 1B:
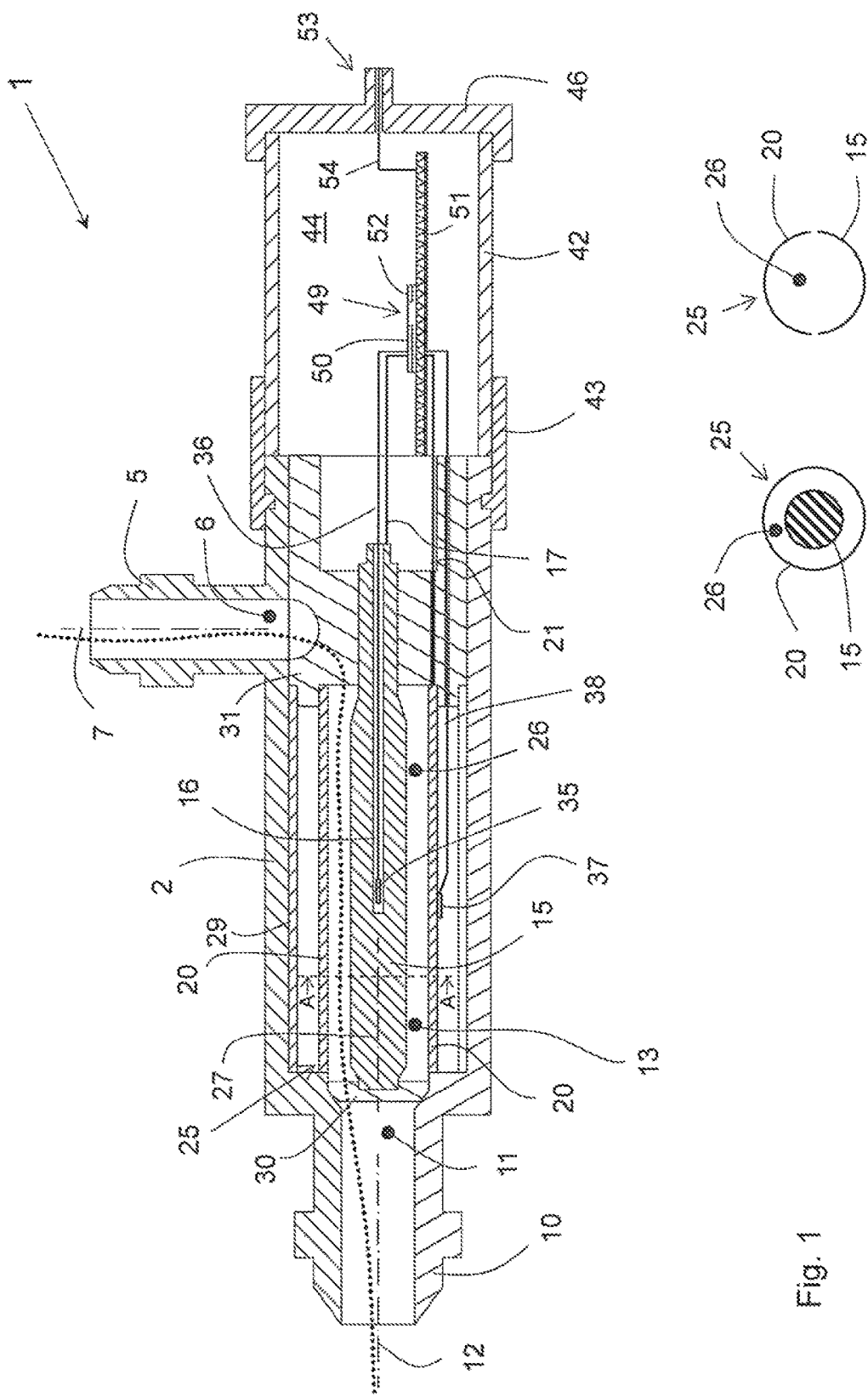
FIG. 1 a longitudinal section of an oil quality sensor according to the invention.
FIG. 1a a cross section through the oil quality sensor of FIG. 1 along the A-A line.
FIG. 1b a cross section through an alternative embodiment of an oil quality sensor.

Reference will now be made to embodiments of the invention, one or more examples of which are shown in the drawings. Each embodiment is provided by way of explanation of the invention, and not as a limitation of the invention. For example features illustrated or described as part of one embodiment can be combined with another embodiment to yield still another embodiment. It is intended that the present invention include these and other modifications and variations to the embodiments described herein.

FIG. 1 shows an oil quality sensor 1 according to the invention in longitudinal section. It has a housing 2, in which a hollow space 13 is provided. A flange 5, mounted on the hollow space 13 at a right angle, has an inlet opening 6 for introducing deep-frying oil. On the other hand, in the extension of the housing 2, another flange 10 has been mounted on the drain opening 11 through which the deep-frying oil can leave the hollow space 13. The inlet and drain openings 6, 11, which have advantageously a round cross section, have in each case a middle axis 7 or 12, and these two axes 7, 12 run perpendicularly to one another.

In the hollow space 13, along its longitudinal axis 27, the front and back sides of an elongated first electrode 15 are mounted in a front or rear centering element 30, 31, respectively. A second electrode 20 that also extends in longitudinal direction of the hollow space 13 has been arranged around the first electrode 15 in the circumferential direction, so that the external side of the first electrode 15 and the internal side of the second electrode 20 lie opposite and are separated from one another. Both the first and the second electrode 15, 20 are executed to have a circular cross section and arranged concentrically to each other, see the cross section drawing in FIG. 1a. Together, they form a capacitor 25 with a space 26 located between the electrodes 15, 20 that is part of the hollow space 13. Deep-frying oil, which flows through the inlet opening 6 and to the oil quality sensor 1, then flows through the space 26 towards the drain opening 11 (indicated by the dotted line, here shown as flow along an upper flow-through path).

A shell-shaped, elongated and metallic shield electrode 29 electrically insulated from the housing 2 with a circular cross section and mounted tightly against the internal side of the housing 2 and likewise running along the hollow space 13 is arranged concentrically with respect to the above-mentioned electrodes 15, 20 and surrounds them. The shield electrode 29, which is arranged at a distance from the second electrode 20, serves to shield from interference signals wanting to penetrate from the outside. Owing to the insulation from the housing 2, another electrical potential can be employed for the shielding action than the electrical mass of the housing 2. This is advantageous, for example, when the housing 2 is on ground potential (which is generally the case when installed in deep fryers). As a result of this, interferences from the ground can be transferred to the housing mass under certain circumstances.

A first temperature sensor 35 (e.g. PT1000) is inserted in a hollow section 16 of the first electrode 15, in which case the hollow section is formed by a blind hole running along the longitudinal axis 27 of the capacitor (which coincides with the longitudinal axis 27 of the hollow space 13).

A second temperature sensor 37 (likewise PT1000 for example) is provided on the external side of the second electrode 20 for measuring the temperature there.

The two temperature sensors 35, 37, each one arranged more or less in the middle of the two electrodes 15, 20, provide measured temperature values from which an average temperature is determined that provides a more accurate indication of the temperatures prevailing inside the oil quality sensor 1. In particular, the temperature gradient that prevails between the first and second electrode 15, 20 can be accounted for. Since the temperature is directly included in the calculation of the polar fractions—together with the measured capacitance of the capacitor 25, in which the deep-frying oil forms the dielectric material—, a rather precise determination of an effective temperature is desired.

The two electrodes 15, 20 are connected to an electronic measurement system 49 arranged on a board 51 through electric wires 17 and 21. The board 51 is fastened to a chamber 44 formed by a rear housing 42 and the former is located on the end of the hollow space 13 opposite the drain opening 11 and connected to the housing 2 with a ring-shaped adapter 43. The two temperature sensors 35, 37 are also connected to the electronic measurement system 49 with electrical wires 36 and 38. To guide the electrical wires 17, 21, 36, 38 to the electronic measurement system 49, the corresponding openings have been provided in the rear centering element 31.

An evaluation unit 50, here a part of the electronic measurement system 49, is provided to record the measured capacitances and measured temperatures, as well as to digitalize the measured values and calculate the polar fractions. Furthermore, an electronic storage element 52 is arranged on the board 51—either as separate element or as part of the electronic measurement system 49—in which correlation functions (which display the relationship between the capacitance values and the different types of deep-frying oil) are stored. This design enhances measurement accuracy because each type of deep-frying oil has a different dielectric constant.

The chamber 44, closed in the rear by a covering cap 46, is provided with a digital interface 53 in form of a USB connection, for example, for emitting signals of the evaluation unit 50, for storing new correlation functions, programming measurement cycles of the electronic measurement system 49 or the like.

As mentioned above, FIG. 1 shows the middle axis 7 of the inlet opening 6 ending in the hollow space 13 at a right angle. This opens up the possibility of connecting the electrical wires 17, 21, 36, 38 easily, as they can now be guided by and large linearly into the rear chamber 44, as described above. If, on the other hand, the middle axes 7, 12 would lie parallel or even coaxially to one another, it would be a lot harder to guide these electrical wires 17, 21, 36, 38 and put the electronic measurement system 49 in place.

In an alternative embodiment shown schematically in cross section in FIG. 1b (cf. FIG. 1a), the capacitor 25 is executed as a tube capacitor in which the two electrodes 15, 20 are executed as half shells whose concave surfaces lie opposite one another by forming a space 26 through which the deep-frying oil can be guided through.

Figure 3:
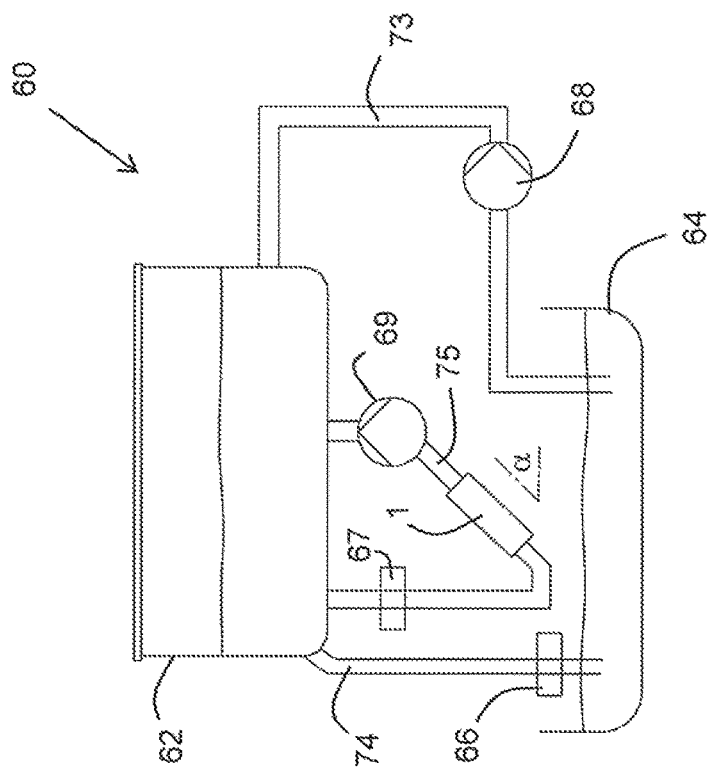
Figure 2:
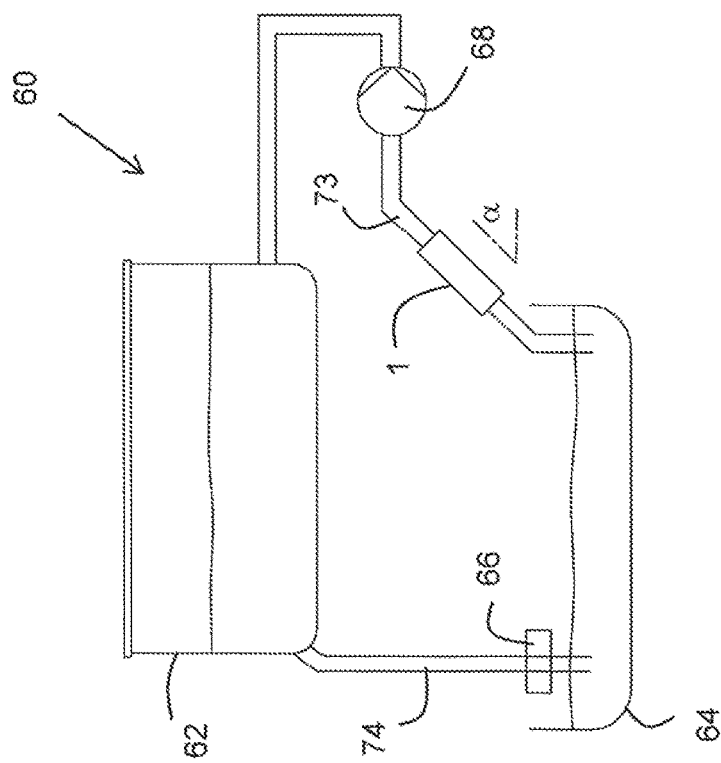
FIG. 2 a schematic diagram of the first possible arrangement of the oil quality sensor in a deep fryer, and FIG. 3 a schematic diagram of the second possible arrangement of the oil quality sensor in a deep fryer.

FIGS. 2 and 3 show very schematically two embodiments of a deep fryer 60, in which a deep fryer basin 62 for deep-frying food is connected to a deep fryer tank 64 through supply and drain lines 73, 74. A filtering device 66 to filter the deep-frying oil for separating the deep-frying remainders and other impurities has been installed here in the drain line 74. A pump 68 has been integrated into the supply line 73 to which the oil quality sensor 1 according to the invention has been connected upstream. It is arranged at an angle (here approx. 45° to the horizontal), so after closing a valve (not shown) or turning off the pump and waiting a short time for the oil to calm down in the oil quality sensor 1, air and water vapor can escape upward from the drain opening 11 and water can deposit in the lower part of the oil quality sensor 1 underneath the space 26.

In FIG. 3, the oil quality sensor 1 is installed in a line 75 of a secondary cycle (i.e. outside the deep-frying cycle) so the secondary cycle can also be named measuring cycle. A filtering device 67 and a pump 69 are also available in the secondary cycle.

The lines 73 and 75 that lead to and away from the oil quality sensor have largely the same flow-through cross section as its inlet and drain opening 6, 11 to prevent above all turbulence or other flowing disturbances. Preferred are cross section deviations of less than 25%.

The oil quality sensor allows not only the measurement of the polar fractions in the deep-frying oil and therefore its quality but also—as described above—the presence of air and the fill level of the deep fryer tank 64 (the control device of the deep fryer 60 shown here is not shown in the figures).

Modifications and variations can be made to the embodiments illustrated or described herein without departing from the scope and spirit of the invention as set forth in the appended claims.

LIST OF REFERENCE CHARACTERS

1 Oil quality sensor
2 Housing
5 Flange
6 Inlet opening
7 Middle axis of the inlet opening
10 Flange
11 Drain opening
12 Middle axis of the drain opening
13 Hollow space
15 First electrode
16 Hollow section
17 Wire of the first electrode
20 Second electrode
21 Wire of the second electrode
25 Capacitor
26 Space
27 Longitudinal axis of the capacitor or hollow space
29 Shield electrode
30 Front centering element
31 Rear centering element
35 First temperature sensor
36 Wire of the first temperature sensor
37 Second temperature sensor
38 Wire of the second temperature sensor
42 Rear housing
43 Adapter
44 Chamber
46 Covering cap
49 Electronic measurement system
50 Evaluation unit
51 Board
52 Electronic storage unit
53 Interface
60 Deep fryer
62 Deep fryer basin
64 Deep fryer tank
66 Filtering device
67 Filtering device
68 Pump
69 Pump
73 Supply line
74 Drain line
75 Wire

The invention claimed is:

1. An oil quality sensor to determine the quality of deep-frying oil by measuring capacitance of the deep-frying oil in a deep fryer, comprising:
   a housing defining a longitudinally extending hollow space through which the deep-frying oil is guided;
   an inlet opening in the housing to introduce deep-frying oil into the hollow space;
   a drain opening in the housing to drain the deep-frying oil out of the hollow space;
   a first electrode that extends longitudinally within the hollow space;
   a second electrode that extends longitudinally within the hollow space and arranged concentric with the first electrode, wherein the first and second electrodes form a tube capacitor, the first and second electrodes comprising half shells with concave surfaces that lie opposite one another and define a space therebetween through which the deep-frying oil is guided to measure capacitance of the deep-frying oil;
   a first temperature sensor disposed in the hollow space to measure temperature of the deep-frying oil; and
   an evaluation unit that records and digitalizes the measured capacitance from the capacitor and the measured temperature, and calculates polar fractions in the deep-frying oil by using the measured capacitance and measured temperature, wherein the polar fractions indicate quality of the deep-frying oil.

2. The oil quality sensor according to claim 1, wherein the capacitor comprises a cylinder capacitor, the second electrode surrounding the first electrode with the space defined between the first and second electrode through which the deep-frying oil is guided.

3. The oil quality sensor according to claim 1, further comprising a shield electrode provided around the first and second electrodes to protect the first and second electrodes from outside interfering signals.

4. The oil quality sensor according to claim 1, wherein a middle axis of the inlet opening extends at an angle of 90° to a longitudinal axis of the capacitor.

5. The oil quality sensor according to claim 4, wherein electric wires for the first and second electrodes and for the first temperature sensor run in an axial direction of the capacitor.

6. The oil quality sensor according to claim 5, wherein a middle axis of the drain opening runs parallel to the longitudinal axis of the capacitor.

7. The oil quality sensor according to claim 1, further comprising a chamber is disposed at a front side of the hollow space, the evaluation unit and a digital interface located in the chamber, wherein the evaluation unit is connected by electrical wires to the first and second electrodes and the first temperature sensor.

8. The oil quality sensor according to claim 1, further comprising an electronic storage unit in communication with the evaluation unit, the electronic storage unit having stored correlation functions are stored that provide a correlation between the capacitance measured values and different types of oil, wherein the electronic storage unit uses the correlation functions to calculate the polar fractions from the measured capacitance and temperature.

9. An oil quality sensor to determine the quality of deep-frying oil by measuring capacitance of the deep-frying oil in a deep fryer, comprising:
 a housing defining a hollow space through which the deep-frying oil is guided;
 an inlet opening in the housing to introduce deep-frying oil into the hollow space;
 a drain opening in the housing to drain the deep-frying oil out of the hollow space;
 a first electrode that extends along the hollow space;
 a second electrode that extends along the hollow space and arranged opposite the first electrode, wherein the first and second electrodes form a capacitor and the deep-frying oil is guided through a space formed between the first and second electrodes to measure capacitance of the deep-frying oil;
 a first temperature sensor disposed in the hollow space closet to the first electrode to measure temperature of the deep-frying oil;
 an evaluation unit that records and digitalizes the measured capacitance from the capacitor and the measured temperature, and calculates polar fractions in the deep-frying oil by using the measured capacitance and measured temperature, wherein the polar fractions indicate quality of the deep-frying oil; and
 further comprising a second temperature sensor, disposed close to the second electrode and spaced from the first temperature sensor in the hollow space, the evaluation unit computing an average temperature of the deep-frying oil from measured temperatures of the first and second temperature sensors.

10. The oil quality sensor according to claim 9, wherein the first temperature sensor is disposed in direct proximity to the first electrode, and the second temperature sensor is disposed in direct proximity to the second electrode.

11. The oil quality sensor according to claim 10, wherein the capacitor comprises a cylinder capacitor, the second electrode surrounding the first electrode with the space defined between the first and second electrode through which the deep-frying oil is guided, the first temperature sensor arranged inside a hollow section of the first electrode and the second temperature sensor arranged on an external side of the second electrode that faces away from the first electrode.

12. A deep fryer system, comprising:
 a fryer basin to receive deep-frying oil for deep-frying of foods;
 a fryer tank connected to the fryer basin through a supply line and a drain line;
 a filtering device to filter the deep-frying oil located in one of the supply or drain line, the fryer basin, or the fryer tank;
 a pump disposed to transport the deep-frying oil through the supply and drain lines, the fryer basin, and the fryer tank;
 an oil quality sensor installed in a line that transports the deep-frying oil, wherein the oil quality sensor further comprises:
  a housing defining a longitudinally extending hollow space through which the deep-frying oil is guided;
  an inlet opening in the housing to introduce deep-frying oil into the hollow space;
  a drain opening in the housing to drain the deep-frying oil out of the hollow space;
  a first electrode that extends longitudinally within the hollow space;
  a second electrode that extends longitudinally within the hollow space and arranged concentric with the first electrode, wherein the first and second electrodes form a capacitor and the deep-frying oil is guided through a space formed between the first and second electrodes to measure capacitance of the deep-frying oil;
  a first temperature sensor disposed in the hollow space to measure temperature of the deep-frying oil; and
  an evaluation unit that records and digitalizes the measured capacitance from the capacitor and the measured temperature, and calculates polar fractions in the deep-frying oil by using the measured capacitance and measured temperature, wherein the polar fractions indicate quality of the deep-frying oil; and
  wherein the oil quality sensor has a flow-through cross section that deviates no more than 25% from the line transporting the deep-frying oil to and away from the oil quality sensor.

13. The deep fryer according to claim 12, wherein the oil quality sensor is installed in a cycle that comprises a filtering device or in a secondary measuring cycle provided expressly for cycling the deep-frying oil through the oil quality sensor.

14. The deep fryer according to claim 12, wherein the oil quality sensor is disposed such that a longitudinal axis of the capacitor forms an angle with horizontal within the range of 20° to 90°.

15. The deep fryer according to claim 12, wherein the oil quality sensor and the evaluation unit are configured to detect how many times specified threshold values of the measured capacitance are exceeded or not reached within a specified time, and further comprising a control device of the deep fryer in communication with the evaluation unit and configured to conclude from fluctuations in the measured capacitance values relative to the threshold values whether there is air in the deep-fryer system and, if so, generate an alarm or maintenance signal.

16. The deep fryer according to claim 12, wherein the oil quality sensor and the evaluation unit are configured to detect how many times specified threshold values of the measured capacitance are exceeded or not reached within a specified time, and further comprising a control device of the deep fryer in communication with the evaluation unit and configured to conclude from fluctuations in the measured capacitance values relative to the threshold values whether oil flow through the oil quality sensor has been interrupted and, if so, generate an alarm or maintenance signal.

17. A method for measuring quality of deep-frying oil in a deep fryer with an oil quality sensor installed in the deep fryer, wherein the oil quality sensor comprises:
   a housing defining a longitudinally extending hollow space through which the deep-frying oil is guided;
   an inlet opening in the housing to introduce deep-frying oil into the hollow space;
   a drain opening in the housing to drain the deep-frying oil out of the hollow space;
   a first electrode that extends longitudinally within the hollow space;
   a second electrode that extends longitudinally within the hollow space and arranged concentric with the first electrode, wherein the first and second electrodes form a capacitor and the deep-frying oil is guided through a space formed between the first and second electrodes to measure capacitance of the deep-frying oil, wherein a longitudinal axis of the capacitor forms an angle with horizontal within the range of 20° to 90°;
   a first temperature sensor disposed in the hollow space to measure temperature of the deep-frying oil; and
   an evaluation unit that records and digitalizes the measured capacitance from the capacitor and the measured temperature, and calculates polar fractions in the deep-frying oil by using the measured capacitance and measured temperature, wherein the polar fractions indicate quality of the deep-frying oil;

the method further comprising:
   supplying deep-frying oil to the oil quality sensor until the sensor is filled entirely with the deep-frying oil;
   topping the supply of the deep-frying oil to the oil quality sensor;
   waiting for a time sufficient for air, water vapor, and water to escape from the space between the first and second electrodes of the oil quality sensor; and
   subsequently measuring capacitance of deep-frying oil in the oil quality sensor.

18. The method according to claim 17, comprising detecting with the oil quality sensor and the evaluation unit how many times specified threshold values of the measured capacitance are exceeded or not reached within a specified time; and further comprising using a control device of the deep fryer in communication with the evaluation unit and configured to conclude from fluctuations in the measured capacitance values relative to the threshold values whether there is air in the deep-fryer system and, if so, generate an alarm or maintenance signal.

19. The method according to claim 17, comprising detecting with the oil quality sensor and the evaluation unit how many times specified threshold values of the measured capacitance are exceeded or not reached within a specified time, and further comprising using a control device of the deep fryer in communication with the evaluation unit and configured to conclude from fluctuations in the measured capacitance values relative to the threshold values whether oil flow through the oil quality sensor has been interrupted and, if so, generate an alarm or maintenance signal, or a control signal to turn off a pump that pumps the deep-frying oil.

* * * * *